United States Patent [19]

Nicolaides

[11] 4,075,192

[45] Feb. 21, 1978

[54] NONAPEPTIDES AND METHODS FOR THEIR PRODUCTION

[75] Inventor: Ernest D. Nicolaides, Ann Arbor, Mich.

[73] Assignee: Parke, Davis & Company, Detroit, Mich.

[21] Appl. No.: 805,766

[22] Filed: June 13, 1977

[51] Int. Cl.² ..................... C07C 103/52; A61K 37/00
[52] U.S. Cl. ................... 260/112.5 LH; 260/112.5 R; 424/177
[58] Field of Search ............... 260/112.5 LH; 424/177

[56] References Cited

U.S. PATENT DOCUMENTS 4,005,063  1/1977  Gendrich et al. .......... 260/112.5 LH

*Primary Examiner*—Delbert R. Phillips
*Attorney, Agent, or Firm*—Stephen Raines; Frank S. Chow; David B. Ehrlinger

[57] ABSTRACT

New nonapeptides having the formula pGlu-D-Phe-Trp-Tyr(benzyl)-Ser(benzyl)-D-Ala-Leu-Orn-Pro-Y and Y is amino, lower alkylamino or di(lower alkyl)amino.

5 Claims, No Drawings

NONAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new nonapeptides that are represented by the formula

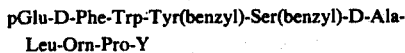

pGlu-D-Phe-Trp-Tyr(benzyl)-Ser(benzyl)-D-Ala-Leu-Orn-Pro-Y     I and Y is amino, lower alkylamino or di(lower alkyl)amino.

The preferred compounds of formula I are those wherein Y is ethylamino or amino.

In formula I, the conventional symbols for amino acid residues of peptide compounds linked thereto are used and each is intended to have the following meaning: Pro, D-prolyl or L-prolyl; Orn, D-ornithinyl or L-ornithinyl; Trp, D-tryptophyl or L-tryptophyl; D-Ala, D-alanyl; pGlu, D-pyroglutamyl or L-pyroglutamyl; Ser, D-seryl or L-seryl; Tyr, D-tyrosyl or L-tyrosyl; Leu, D-leucyl or L-leucyl; Tyr(benzyl), D-tyrosyl(benzyl) or L-tyrosyl(benzyl); Ser(benzyl), D-seryl(benzyl) or L-seryl-(benzyl); and D-Phe, D-phenylalanyl. In addition, the term "lower alkyl" is intended to mean a straight, branched or cyclic hydrocarbon moiety of up to six carbon atoms, such as methyl, ethyl, isopropyl and cyclopropyl. These symbols and terms will also be used in the formulae that follow for other compounds and each such symbol or term should be understood to have the meaning given above.

In accordance with this invention, compounds of the formula I, wherein Y is amino, lower alkylamino or di(lower alkyl)-amino are prepared by reacting a compound of the formula pGlu-D-Phe-Trp-Tyr(benzyl)-Ser(benzyl)-D-Ala-Leu-Arg(nitro)-Pro-Z     II wherein Z is lower alkoxy, preferably methoxy, with ammonia, lower alkylamine or di(lower alkyl)amine.

The term "lower alkoxy" is intended to mean an alkoxy group having a straight, branched or cyclic hydrocarbon moiety of up to six carbon atoms, such as methoxy, ethoxy and isopropoxy.

The reactions are conducted at temperatures of from about 5° to 100° C. for from 3 hours to 4 days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

Compounds wherein Z is lower alkoxy, are produced by removing a protected nonapeptide from a resin complex of the following structure

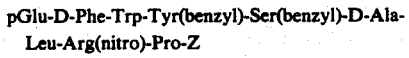

pGlu-D-Phe-Trp-Tyr(benzyl)-Ser(benzyl)-D-Ala-Leu-Arg(nitro)-Pro-resin     III wherein said resin is a resin employed in solid phase peptide syntheses, such as those disclosed in a text by Stewart and Young, "Solid Phase Peptide Synthesis," W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the nonapeptide through a methyleneoxy bridge wherein the methylene group is attached to the polymeric portion of the resin and the oxygen atom is attached to the nonapeptide and Arg is D-Arginyl or L-Arginyl; by treating said resin of the formula III with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

Compounds of the formula I wherein Y is amino, lower alkylamino or di(lower alkyl)amino may also be prepared by reacting compounds of the formula III with ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex nonapeptide resins of the formula III are prepared by coupling an amino acid of the formula

pGlu-OH     IV with complex octapeptide resins of the formula

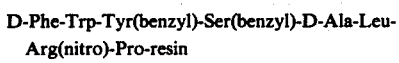

D-Phe-Trp-Tyr(benzyl)-Ser(benzyl)-D-Ala-Leu-Arg(nitro)-Pro-resin     V in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about 15 minutes to about 20 hours.

The complex octapeptide resins of the formula V are prepared by treating octapeptide resins of the formula

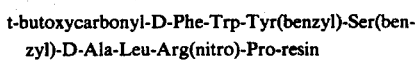

t-butoxycarbonyl-D-Phe-Trp-Tyr(benzyl)-Ser(benzyl)-D-Ala-Leu-Arg(nitro)-Pro-resin     VI with a large excess of trifluoroacetic acid utilizing dichloromethane as the solvent at temperatures of from 20° to 30° C. for about 10 minutes followed by neutralization of the trifluoroacetic acid salt with a base such as triethylamine.

The complex octapeptide resins of the formula VI are prepared by coupling

t-butoxycarbonyl-D-Phe-OH to complex heptapeptide resins of the formula

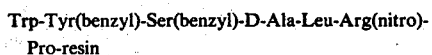

Trp-Tyr(benzyl)-Ser(benzyl)-D-Ala-Leu-Arg(nitro)-Pro-resin     VII using the reaction procedure described for the preparation of compounds of the formula III.

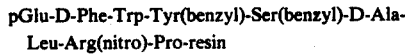

The complex heptapeptide resins of the formula VII are prepared by treating the complex heptapeptide resins of the formula t-butoxycarbonyl-Trp-Tyr(benzyl)-Ser(benzyl)-D-Ala-Leu-Arg(nitro)-Pro-resin      VIII with trifluoroacetic acid using the reaction procedure for the preparation of compounds of the formula V.

The complex heptapeptide resins of the formula VIII are prepared by coupling t-butoxycarbonyl-Trp-OH to complex hexapeptide resins of the formula Tyr(benzyl)-Ser(benzyl)-D-Ala-Leu-Arg(nitro)-Pro-resin      XIX using the reaction procedure described for the preparation of compounds of the formula III.

The complex hexapeptide resins of the formula XIX are prepared by treating the complex hexapeptide resins of the formula t-butoxycarbonyl-Tyr(benzyl)-Ser(benzyl)-D-Ala-Leu-Arg(nitro)-Pro-resin      X with trifluoroacetic acid using the reaction procedure for the preparation of compounds of the formula V.

Complex hexapeptides resins of the formula X are prepared by coupling t-butoxycarbonyl-Tyr(benzyl)—OH to complex resins of the formula Ser(benzyl)-D-Ala-Leu-Arg(nitro)-Pro-resin      XI according to the procedure used for the preparation of compounds of formula III.

The complex resins of the formula XI are prepared by treating the complex resins of the formula t-butoxycarbonyl-Ser(benzyl)-D-Ala-Leu-Arg(nitro)-Pro-resin      XII with trifluoroacetic acid using the reaction procedure for the preparation of compounds of the formula V.

The complex resins of the formula XII are prepared by coupling t-butoxycarbonyl-Ser(benzyl)—OH to complex resins of the formula D-Ala-Leu-Arg(nitro)-Pro-resin      XIII according to the procedure used for the preparation of compounds of formula III.

The complex resins of the formula XIII are prepared by treating the complex resins of the formula t-butoxycarbonyl-D-Ala-Leu-Arg(nitro)-Pro-resin      XIV with trifluoroacetic acid using the reaction procedure for the preparation of compounds of the formula V.

The complex resins of formula XIV are prepared by coupling t-butoxycarbonyl-D-Ala-OH to complex resins of the formula Leu-Arg(nitro)-Pro-resin      XV according to the procedure used for the preparation of compounds of formula III.

The complex resins of the formula XV are prepared by treating the complex resins of the formula t-butoxycarbonyl-Leu-Arg(nitro)-Pro-resin      XVI with trifluoroacetic acid using the reaction procedure for the preparation of compounds of formula V.

The complex resins of formula XVI are prepared by coupling t-butoxycarbonyl-Leu-OH to a complex resin of the formula Arg(nitro)-Pro-resin      XVII according to the procedure used for the preparation of compounds of formula III.

The complex resins of the formula XVII are prepared by treating complex resins of the formula t-butoxycarbonyl-Arg(nitro)-Pro-resin      XVIII with trifluoroacetic acid using the reaction procedure for the preparation of compounds of formula V.

The complex resins of the formula XVIII are prepared by coupling t-butoxycarbonyl-Arg(nitro)-OH to a complex resin of the formula Pro-resin      XIX according to the procedure used for the preparation of compounds of formula III.

The complex resins of the formula XIX are prepared by treating the complex resins of the formula t-butoxycarbonyl-Pro-resin      XX with trifluoroacetic acid using the reaction procedure for the preparation of compounds of the formula V.

The compounds of this invention can exist in anhydrous forms as well as in solvated, including hydrated, forms. In general, the hydrated forms and the solvated forms with pharmaceutically acceptable solvents are equivalent to the anhydrous or unsolvated form for the purposes of the invention.

Nonapeptides of this invention were screened for LRF antagonist activity in vitro using rat anterior pituitary cell cultures as described by Vale et al. [Endocrinology, 91, 562 (1972)]. The inhibition of LRF (luteinizing hormone releasing factor) induced luteinizing hormone (LH) release into the culture medium is the endpoint in this in vitro bioassay.

| ACTIVITY TABLE FOR IN VITRO TEST IN RAT ANTERIOR PITUITARY CELL CULTURES | | | |
| --- | --- | --- | --- |
| Compound | Molar Conc. | LH Value ng./ml. | % LH Release Inhibition |
| L-Pyroglutamyl-D-phenyl-alanyl-L-tryptophyl-O- | | | |

| ACTIVITY TABLE FOR IN VITRO TEST IN RAT ANTERIOR PITUITARY CELL CULTURES | | | |
|---|---|---|---|
| Compound | Molar Conc. | LH Value ng./ml. | % LH Release Inhibition |
| benzyl-L-tyrosyl-O-benzyl-L-seryl-D-alanyl-L-leucyl-L-ornithyl-L-proline N-ethylamide | $1 \times 10^{-6}$ | 19.15 | 61 |
| LRF Control | $2.5 \times 10^{-10}$ | 39.98 | |
| Saline Control | | 6.25 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the nonapeptides of this invention are useful in controlling ovulation and in restricting fertility.

The invention is illustrated by the following examples.

EXAMPLE 1

L-Pyroglutamyl-D-phenylalanyl-L-tryptophyl-O-benzyl-L-tyrosyl-O-benzyl-L-seryl-D-alanyl-L-leucyl-$N^G$-nitro-L-arginyl-L-proline resin, 12.5 g., is stirred in 200 ml. of methanol and 20 ml. of triethylamine for 2 days. After filtration and evaporation, 2.5 g. of L-pyroglutamyl-D-phenylalanyl-L-tryptophyl-O-benzyl-L-tyrosyl-O-benzyl-L-seryl-D-alanyl-L-leucyl-$N^G$-nitro-L-arginyl-L-proline methyl ester is obtained after precipitation from cooled isopropanol; m.p. 174°–175° C. The previous methyl ester, 0.7 g., is treated with 10 ml. of ethylamine and 20 ml. of methanol and 5 ml. of dimethylformamide at 25° C. for 3 days. After evaporation, 0.4 g. of L-pyroglutamyl-D-phenylalanyl-L-tryptophyl-O-benzyl-L-tyrosyl-O-benzyl-L-seryl-D-alanyl-L-leucyl-L-ornithyl-L-proline N-ethylamide is obtained after three times precipitating the product from cooled isopropanol as a dihydrate; m.p. 160°–165° C.

L-Pyroglutamyl-D-phenylalanyl-L-tryptophyl-O-benzyl-L-tyrosyl-O-benzyl-L-seryl-D-alanyl-L-leucyl-$N^G$-nitro-L-arginyl-L-proline resin is prepared according to the General Procedure, given below, from 50 g., 0.040 mol., of $N^\alpha$-t-butoxycarbonyl-L-proline resin by successive coupling with 1) 15.0 g., 0.047 mol., of $N^\alpha$-t-butoxycarbonyl-$N^G$-nitro-L-arginine and 10.0 g., 0.049 mol., of dicyclohexylcarbodiimide, 2) 11.0 g., 0.044 mol., of $N^\alpha$-t-butoxycarbonyl-L-leucine hydrate and 10.0 g., 0.049 mol., of dicyclohexylcarbodiimide, 3) 9.0 g., 0.048 mol., of $N^\alpha$-t-butoxycarbonyl-D-alanine and 10.0 g., 0.049 mol., of dicyclohexylcarbodiimide, 4) 14.0 g., 0.046 mol., of $N^\alpha$-t-butoxycarbonyl-O-benzyl-L-serine and 10.0 g., 0.049 mol., of dicyclohexylcarbodiimide, 5) 17.5 g., 0.047 mol., of $N^\alpha$-t-butoxycarbonyl-O-benzyl-L-tyrosine and 10.0 g., 0.049 mol., of dicyclohexyl-carbodiimide, 6) 15.0 g., 0.049 mol., of $N^\alpha$-t-butoxycarbonyl-L-tryptophan and 10.0 g., 0.049 mol., of dicyclohexylcarbodiimide, 7) 11 g. of the resin obtained in step 6 was reacted with 2.0 g., 0.0075 mol., of $N^\alpha$-t-butoxycarbonyl-D-phenylalanine and 1.6 g., 0.0078 mol., of dicyclohexylcarbodiimide, 8) 1.5 g. 0.0116 mol., of L-pyroglutamic acid and 1.6 g., 0.0078 mol., of dicyclohexylcarbodiimide.

$N^\alpha$-t-Butoxycarbonyl-L-proline resin is obtained by refluxing 50 g., 0.058 mol., of 1% chloromethylated resin, 14 g., 0.065 mol., of $N^\alpha$-t-butoxycarbonyl-L-proline and 8.7 g., 0.086 mol., of triethylamine in 300 ml. of absolute ethanol for 2 days. Nitrogen analysis shows 0.00085 mol. per gram.

GENERAL PROCEDURE FOR THE SOLID PHASE SYNTHESIS OF PEPTIDE RESINS

The peptide resin is obtained by attaching an α-amino-protected amino acid to a resin (usually a chloromethylated resin which is commercially available from Lab Systems. Inc., San Mateo, Calif.). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart, "Solid Phase Peptide Synthesis," W. H. Freeman and Co., 1969.

Each cycle of the procedure follows the scheme:

1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to 30 minutes agitation with the α-amino-protected amino acid which is present in up to a fourfold molar excess based on the resin nitrogen analysis. However, when a large excess of the α-amino-protected amino acid is used it is agitated with the resin for 15 minutes and the excess recovered by draining the solution from the reactor.
6. Addition of dicyclohexylcarbodiimide at least equivalent to the α-amino-protected amino acid in step 5 in dichloromethane followed by agitation for 4 to 20 hours. In the alternate method, a 3.3-fold excess of dicyclohexylcarbodiimide is used relative to the α-amino-protected amino acid resin.
7. Three washes with dichloromethane.

I claim:

1. A nonapeptide of the formula

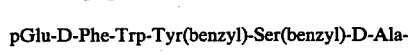
pGlu-D-Phe-Trp-Tyr(benzyl)-Ser(benzyl)-D-Ala-Leu-Orn-Pro-Y wherein Y is amino, lower alkylamino or di(lower alkyl)amino.

2. The nonapeptides of claim 1 wherein Y is amino or ethylamino.

3. The nonapeptide of claim 1 having the name L-pyroglutamyl-D-phenyl-alanyl-L-tryptophyl-O-benzyl-L-tyrosyl-O-benzyl-L-seryl-D-alanyl-L-leucyl-L-ornithyl-L-proline N-ethyl-amide.

4. A process for the production of a compound of the formula

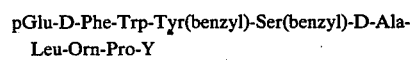
pGlu-D-Phe-Trp-Tyr(benzyl)-Ser(benzyl)-D-Ala-Leu-Orn-Pro-Y which comprises reacting a compound of the formula pGlu-D-Phe-Trp-Tyr(benzyl)-Ser(benzyl)-D-Ala-
Leu-Orn-Pro-O-lower alkyl with ammonia, lower alkylamine or di(lower alkyl)amine wherein Y is as described in claim 1.

5. A process for the production of a compound of the formula pGlu-D-Phe-Trp-Tyr(benzyl)-Ser(benzyl)-D-Ala-
Leu-Orn-Pro-Y which comprises reacting a compound of the formula pGlu-D-Phe-Trp-Tyr(benzyl)-Ser(benzyl)-D-Ala-
Leu-Orn-Pro-resin with ammonia, lower alkylamine or di(lower alkyl)amine wherein Y is as described in claim 1.

* * * * *